United States Patent [19]
Bourdauducq

[11] Patent Number: 6,040,456
[45] Date of Patent: Mar. 21, 2000

[54] PROCESS FOR THE PREPARATION OF 4-AMINO-1,2,4-TRIAZOLE

[75] Inventor: Paul Bourdauducq, Chaponost, France

[73] Assignee: Elf Atochem S.A., France

[21] Appl. No.: 08/965,144

[22] Filed: Nov. 6, 1997

[30] Foreign Application Priority Data

Nov. 7, 1996 [FR] France .................................. 96 13590

[51] Int. Cl.[7] .............................................. C07D 249/08
[52] U.S. Cl. ....................................................... 548/265.6
[58] Field of Search ......................................... 548/265.6

[56] References Cited

U.S. PATENT DOCUMENTS 5,099,028   3/1992   Goe et al. .

FOREIGN PATENT DOCUMENTS 0 269 308   6/1988   European Pat. Off. .
2 036 912   6/1995   Russian Federation .

OTHER PUBLICATIONS

Nasu et al., "Preparation of 4–Amino–1,2,4–triazole," CA 118: 124567 (1992).
Cram and Hammond, "Organic Chemistry", McGraw Hill Book Co., NY (1964) 2nd. Edition. pp. 565–567.
"Studies on the Formation of 4–Aminotriazole Derivatives from Acyl Hydrazides", Robert M. Herbst, et al., *Journal of Organic Chemistry 18*: pp. 872–877 (Jul. 1953).
Chemical Abstracts No. 9197g, Kost, et al., "Reactions of Hydrazine Derivatives. XIX. Condensations of 4–amino–1, 2,4–triazole with Esters", vol. 53, No. 10, (May 25, 1959).
"Catalogue Handbook of Fine Chemicals", product A8, 180–3, Aldrich, p. 97 (1994).

*Primary Examiner*—Patricia L. Morris

[57] ABSTRACT

The present invention relates to a process for the preparation of products of formula (1):

$$\underset{NH_2}{\underset{|}{R-C}}\overset{N=N}{\underset{N}{\parallel}}C-R \quad (1)$$

in which R denotes H or an alkyl group containing from 1 to 10 carbon atoms, it being possible for this alkyl group to be substituted by one or more aryl, heteroaryl, hydroxyl or alkenyl groups, in which process hydrazine is reacted with a deficiency of carboxylic acid RCOOH and then the water of reaction and optionally the water of dilution of the hydrazine and of the acid is removed.

It is particularly useful for preparing 4-amino-1,2,4-triazole.

4 Claims, No Drawings

PROCESS FOR THE PREPARATION OF 4-AMINO-1,2,4-TRIAZOLE

FIELD OF THE INVENTION

The present invention relates to a process for the preparation of 4-amino-1,2,4-triazole and more particularly products having the following formula:

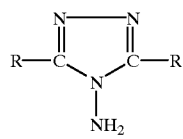
(1)

in which R denotes H or an alkyl group containing from 1 to 10 carbon atoms, it being possible for this alkyl group to be substituted by one or more aryl, heteroaryl, hydroxyl or alkenyl groups. Both R could be the same or different.

It consists in reacting hydrazine with a deficiency of carboxylic acid RCOOH and in then removing, by distillation, the water of reaction and optionally the water of dilution of the hydrazine and of the acid.

BACKGROUND OF THE INVENTION

A description has been given in the prior art, U.S. Pat. No. 5,099,028, of a process for the preparation of the same 4-amino-1,2,4-triazoles of formula (1) in which the reaction of the acid RCOOH with the hydrazine is carried out in the presence of an insoluble polymer containing acid functional groups, that is to say an ion-exchange resin.

For products of formula (1) in which R is H, that is to say 4-amino-1,2,4-triazole, the prior art makes it possible to obtain, after recrystallization from isopropanol, a yield of 85% and a purity of 99.5%, if the resin is not recycled, or a yield of 91% and a purity of 99.4%, if the resin is recycled (% by weight).

DESCRIPTION OF THE INVENTION

Applicant has discovered that it is not necessary to carry out the preparation in the presence of resins and, moreover, that, by using the process of the invention, the formation of an impurity of formula (2) is greatly decreased:

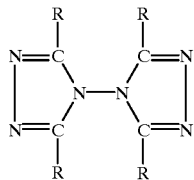
(2)

Moreover, after recrystallization, a product (1) of high purity is obtained. For example, for the product in which R is H, the purity is at least 99.9% (by weight).

The invention is particularly useful for preparing the product of formula (1) in which R is H, that is to say 4-amino-1,2,4-triazole.

The present invention also relates to a product of formula (1) having a purity of greater than 98.5%, advantageously of greater than 99.5% and preferably of greater than 99.9% (by weight).

The hydrazine can be anhydrous or in the hydrate form $N_2H_4 \cdot H_2O$, optionally in aqueous solution. It is sufficient to use the hydrate $N_2H_4 \cdot H_2O$ in aqueous solution. These solution can, for example, contain from 24 to 100% by weight of $N_2H_4 \cdot H_2O$.

The acid RCOOH can contain up to 20% water. For formic acid HCOOH, use is advantageously made of a product with a purity of more than 90%. The deficiency of acid RCOOH could be 2 to 5% preferably 2 to 3% relating to stoichiometry.

The reaction of the acid with the hydrazine takes place at room temperature and atmospheric pressure, the temperature is allowed to rise as a result of the exothermicity of the reaction and then the reaction mixture is heated at approximately 130–180° C. in order to distil off the water, advantageously under an absolute pressure between 20 and 100 mm Hg (26 and 133 hPa).

It is advantageous to pour the acid into the hydrazine in order to control the exothermicity of the reaction. It is also possible to begin to remove the water from the beginning of the reaction. The reaction can be carried out non-continuously or continuously according to the usual techniques of organic synthesis, which a person skilled in the art will appreciate.

According to an advantageous form of the process, the product (1) is washed in and/or crystallized from a solvent. This solvent is preferably isopropanol.

EXAMPLES

4-Amino-1,2,4-triazole is synthesized by reaction of formic acid with hydrazine hydrate, according to the reaction:

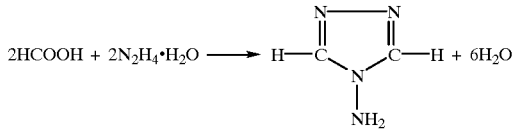

The reaction is carried out with various proportions of formic acid and of hydrazine.

A marked variation in the content of impurity (2) is obtained in the crude products before recrystallization (Table 1).

TABLE 1

| Formic acid | 2.5% Deficiency | 1% Deficiency | Stoichiometry | 5% Excess |
|---|---|---|---|---|
| Analysis by HPLC liquid chromatography of 4,4'-bis(1,2,4-triazole) (weight %) | <0.1 | 0.3 | 1.3 | 4 |

A description is given below of the reaction with a 2.5% deficiency of formic acid, followed by recrystallization from isopropanol.

29.25 mol of formic acid, resulting from a 96% solution, are run in, over 1 h, into 30 mol of hydrazine hydrate resulting from a 99.5% solution, the temperature being allowed to rise to 85° C., and then the reaction mixture is heated for 7 h, while distilling off the water to 170° C., and maintained at 170° C. for 2 h under 50 mm Hg.

The reaction mixture is cooled to 80° C. and 1740 g of isopropanol are added [crude 4-ATA ≈42 weight %].

The mixture is heated at ~75° C. until completely dissolved and allowed to slowly cool with gentle stirring.

The product is filtered off at ≈5° C., washed with 150 g of cold isopropanol and dried.

Weight of cake recovered=1186 g

Dry weight=1008 g

A very pure product is obtained with a crude yield of 82%.

Analysis by HPLC: 99.9%

Chemical quantitative determination by HClO$_4$: 99.7%

Water content: 0.14%

By way of comparison, the same synthesis was carried out with stoichiometric amounts of the reactants.

The following results are obtained (Table 2):

TABLE 2

| Analysis by HPLC liquid chromatography (weight %) | Stoichiometry | Stoichiometry then recrystallization | 2.5% Deficiency of acid | 2.5% Deficiency of acid then recrystallization |
|---|---|---|---|---|
| diformyl-hydrazine | 0.5 | 0.03 | 0.5 | 0.03 |
| monoformyl-hydrazine | 0.5 | 0.01 | 0.4 | 0.01 |
| 1,2,4-triazole | 0.6 | 0.03 | 0.5 | 0.03 |
| 4,4'-bis(1,2,4-triazole) | 1.3 | 1.2 | 0.08 | 0.02 |
| 4-amino-1,2,4-triazole | 97.1 | 98.7 | 98.5 | 99.9 |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

I claim:

1. Process comprising preparation of a product of formula (1):

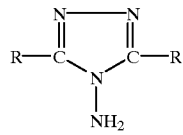

(1)

in which R denotes H or an alkyl group containing from 1 to 10 carbon atoms, optionally substituted by at least one member select from the group consisting of aryl, hydroxyl and alkenyl, wherein said aryl is a carbocyclic aryl of 6 to 10 carbon atoms, comprising the steps of:

a) reacting hydrazine with a deficiency of carboxylic acid RCOOH, wherein the deficiency of carboxylic acid RCOOH is between 2 to 5% relating to stoichiometry, b) removing, by distillation, water of reaction, c) optionally removing water of dilution of the hydrazine and of the acid and d) crystallizing said product.

2. Process according to claim 1, wherein a recrystallization from isopropanol is subsequently carried out.

3. Process according to claim 1, wherein R is H.

4. Process according to claim 1, wherein said product is 4-amino-1,2,4-triazole.

* * * * *